United States Patent [19]

Pastrone

[11] 4,453,932
[45] Jun. 12, 1984

[54] INTRAVENOUS METERING DEVICE

[75] Inventor: Giovanni Pastrone, Los Gatos, Calif.

[73] Assignee: Oximetrix, Inc., Mountain View, Calif.

[21] Appl. No.: 350,361

[22] Filed: Feb. 19, 1982

Related U.S. Application Data

[63] Continuation of Ser. No. 174,666, Aug. 1, 1980, Pat. No. 4,336,800.

[51] Int. Cl.³ .............................................. A61M 5/00
[52] U.S. Cl. .................................... 604/153; 604/123; 417/443; 128/DIG. 12
[58] Field of Search ................ 604/122, 123, 151–153; 417/435, 443; 128/DIG. 12

[56] References Cited

U.S. PATENT DOCUMENTS

| | | | |
|---|---|---|---|
| 3,559,644 | 2/1971 | Stoft et al. | 604/123 |
| 3,874,826 | 4/1975 | Lundquist | 604/123 X |
| 4,030,495 | 6/1977 | Virag | 604/123 |
| 4,140,118 | 2/1979 | Jassawalla | 604/123 |
| 4,142,524 | 3/1979 | Jassawalla et al. | 604/123 |
| 4,336,800 | 6/1982 | Pastrone | 604/123 |

OTHER PUBLICATIONS

Abbott/Shaw Life Care Pump® Model 11/D, No. 7011, Published 7/78.

*Primary Examiner*—Dalton L. Truluck
*Attorney, Agent, or Firm*—Robert S. Kelly

[57] ABSTRACT

A device for precise metering of liquids for intravenous delivery to a patient, the device including a pumping chamber with a reciprocable diaphragm positioned therein. The device also includes check valves positioned at the pumping chamber inlet and outlet, and a gas retention chamber located upstream of the pumping chamber and having an upper portion providing for the formation of a gas-liquid interface and a lower portion from which liquid free of gas bubbles may be removed and directed into the pumping chamber.

7 Claims, 3 Drawing Figures

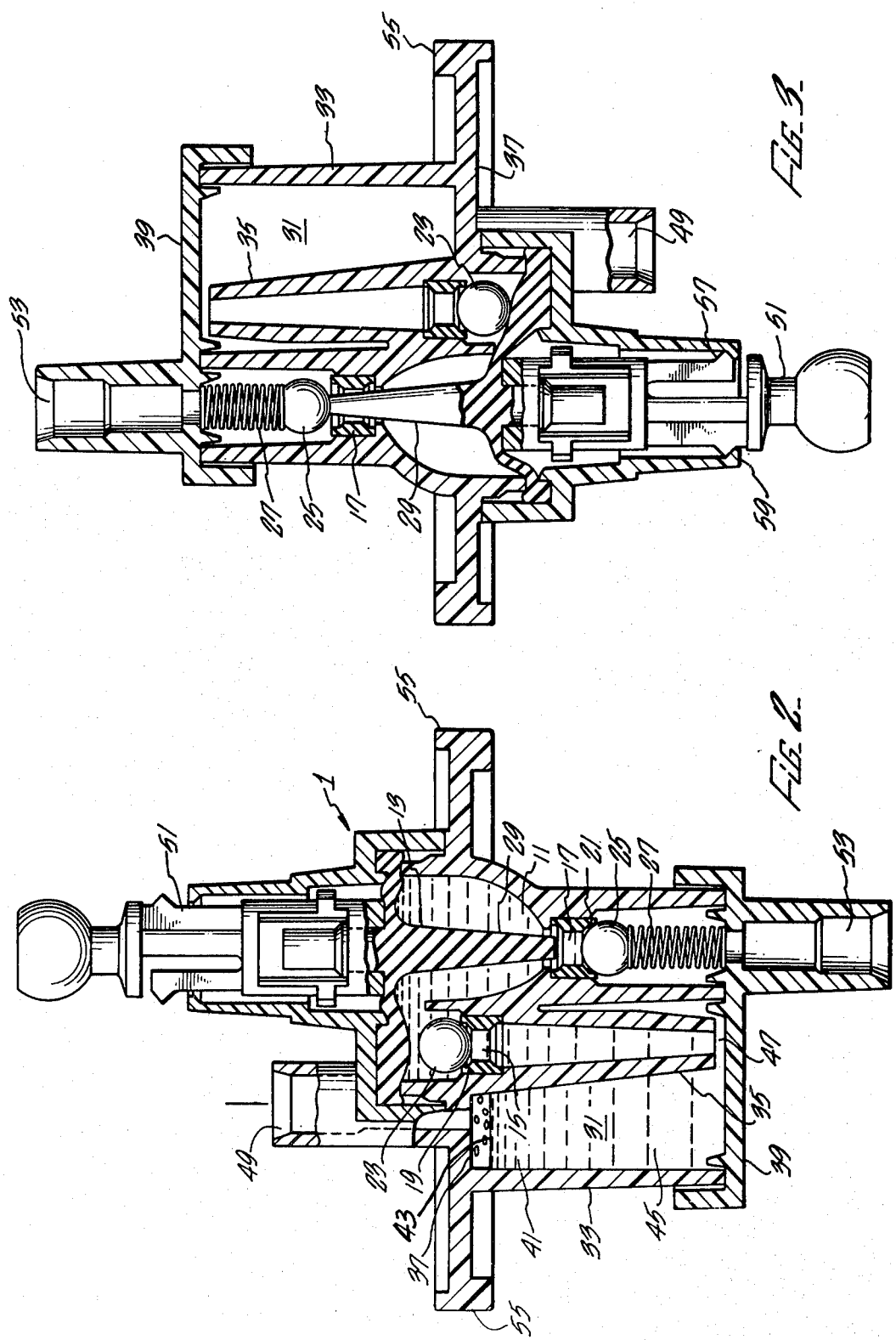

INTRAVENOUS METERING DEVICE

This is a continuation of application Ser. No. 174,666 filed Aug. 1, 1980, now U.S. Pat. No. 4,336,800, issued Jan. 29, 1982.

BACKGROUND OF THE INVENTION

Considerable attention has been directed to intravenous delivery to patients of fluids, such as saline solutions and the like, in the last several years. Initially, such materials were administered to a patient by means of gravity flow from a container containing the liquid to be delivered. A difficulty encountered with such devices was that administration by gravity flow often required that the container for the liquid to be transmitted to the patient had to be positioned at a considerable elevation above the patient. Further, attempts to accurately regulate the flow of such devices proved difficult because of the fact that the pressure causing the flow to be transferred to the patient decreased as the liquid level within the container was reduced during the delivery operation.

SUMMARY OF THE INVENTION

The device of the present invention includes a pumping chamber having a rigid shell and a pair of laterally projecting shoulders that permit the device to be removably inserted into and retained within a control unit in an upright position. The pumping chamber has a biased valve closing an outlet port at the lower end thereof and a valve normally closing an inlet port at the upper end thereof. A diaphragm having an actuator attached thereto forms at least a portion of the upper wall of the chamber with the actuator being adapted to be reciprocated vertically by the control unit in order to pump liquid from the chamber. The chamber has a downwardly tapering smoothly curved cross-sectional configuration and a tangential inlet from the inlet port so that when the chamber is initially charged with liquid, by inverting the chamber and disabling the outlet valve by retaining it in an open position, the liquid will be caused to flow through the inlet port and tangentially into the chamber wherein it will swirl upwardly and through the open outlet port to sweep all air from the chamber.

DRAWINGS

FIGS. 2 and 3 are partial cross-sectional views illustrating the subject matter of this invention.

DESCRIPTION OF PREFERRED EMBODIMENTS

Figure 1:
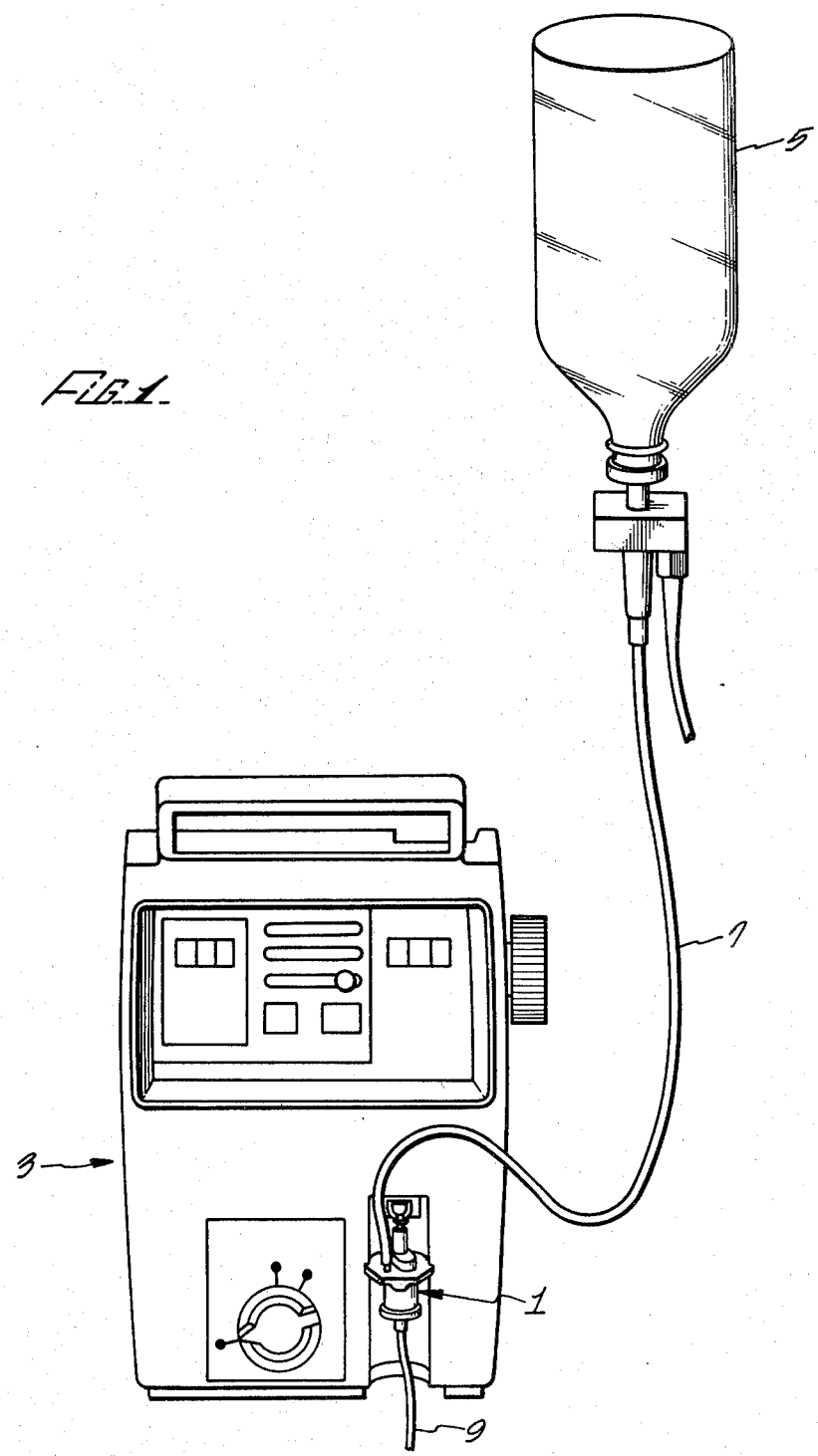
FIG. 1 is a pictorial view illustrating the use of the present invention.

Referring now to FIG. 1, the intravenous metering device 1 is shown positioned within a metering device control unit 3. The intravenous metering device 1 is connected to a container of fluid 5 by means of conventional tubing 7. Tubing 9, extending from the outlet of the intravenous metering device 1 transfers precise amounts of fluid to the patient to be treated.

Referring now to FIG. 2, the construction of the intravenous metering device 1 of the present invention will be discussed in detail. The intravenous metering device 1 will be seen to be of a rigid shell structure and to include a pumping chamber 11 and a reciprocable diaphragm 13 which is positioned within the pumping chamber 11, at the top thereof in the upright operative position as shown in FIG. 2. The intravenous metering device 1 includes a pumping chamber inlet 15 and a pumping chamber outlet 17. Pumping chamber inlet 15 includes a valve seat means 19. Similarly, pumping chamber outlet 17 includes valve seat means 21. Ball checks 23 and 25 are positioned such that they are normally in a position so as to seat against valves seats 19 and 21 of the pumping chamber inlet 15 and pumping chamber outlet 17, respectively. The ball check 23 is normally held in the closed position by gravity while the ball check 25 is normally held in the closed position by biasing means such as spring 27.

The reciprocable diaphragm 13 includes a projection 29, preferably centered within the pumping chamber 11 such that the cross-sectional area of the liquid flow path through the pumping chamber 11 is approximately equal to the cross-sectional area of the pumping chamber inlet 15 and the pumping chamber outlet 17. One of the advantages of this relationship is the relatively constant, high velocities of fluid flow experienced during the initial charging or filling operation of the intravenous metering device 1, which will be discussed in greater detail when reference is made to FIG. 3.

The intravenous metering device 1 further includes a gas retention chamber 31 bounded by a sidewall 33 and gas retention chamber opposed walls 37 and 39. As shown in FIG. 2, the gas retention chamber 31 includes a gas retention chamber upper portion 41 providing for a gas-liquid interface 43, and a gas retention chamber lower portion 45 from whence liquid free of gas bubbles may pass from the gas retention chamber lower portion 45 through a gas retention chamber passageway 47 and into a vertically extending tube 35 to the pumping chamber 11.

The detailed construction of the intravenous metering device 1 of this invention having been described, its method of operation will now be discussed. Incoming fluid, transmitted by tubing such as 7 to the intravenous metering device inlet 49 passes into the gas retention chamber 31 which, due to the relatively large volume thereof, prevents any gases therein from entering the pumping chamber 11 and allows for the generation of a gas-liquid interface 43 in the gas retention chamber upper portion 41. Liquid free of gas bubbles passes from the gas retention chamber lower portion 45 through the tube 35 to the inlet 15. When the intravenous metering device actuator or shaft 51 is reciprocated upwardly, the volume of the pumping chamber 11 is increased by a precise and predetermined amount and the pressure within the pumping chamber 11 correspondingly decreased. This pressure decrease within the pumping chamber 11 is sufficient to lift pumping chamber inlet ball check 23 from pumping chamber inlet valve seat 19 so as to allow the liquid free of gas bubbles to enter the pumping chamber 11. As the reciprocable diaphragm 13 is reciprocated downwardly by means of the intravenous metering device shaft 51, the volume within the pumping chamber 11 is decreased and the pressure within the pumping chamber 11 increased. This increase in pressure within the pumping chamber 11 insures that the pumping chamber chamber inlet ball check 23 will seat against pumping chamber inlet valve seat 19 thus preventing fluid flow from the pumping chamber 11 to the gas retention chamber 31. Furthermore, the increase in pressure within pumping chamber 11 overcomes the biasing means 27 urging pumping chamber outlet ball check 25 to disengage from pumping chamber outlet valve seat 21 thereby allowing a precise amount of metered fluid to be pumped from the pumping chamber 11 through the intravenous metering device outlet 53 to a patient as by means of tubing 9. The intravenous metering device 1 includes laterally projecting shoulders 55 for the positioning and retaining of the intravenous metering device 1 within the metering device control unit 3 that provides control for the reciprocation of the intravenous metering device shaft 51 and the reciprocable diaphragm 13 attached thereto.

FIG. 3 illustrates the orientation and configuration of the intravenous metering device 1 when it is to be filled with liquid to be administered to a patient and placed in service. The intravenous metering device of the present invention may be disposable such that a fresh and sterilized intravenous metering device 1 is employed at each application of intravenous passage of fluid to a patient. As illustrated in FIG. 3, the intravenous metering device 1 is inverted or rotated 180 degrees in order to be filled with liquid. During this filling operation, the intravenous metering device shaft 51 is manually depressed beyond its normal travel length such that intravenous metering device shaft detent 57 is engaged by a corresponding shoulder 59 of the intravenous metering device 1 to lock the shaft in such depressed position. The projection 29 of the reciprocable diaphragm 13 is constructed such that it will then pass through the pumping chamber outlet 17 and engage the outlet ball check 25 to overcome the biasing means 27 acting upon the pumping chamber outlet ball check 25 thereby allowing fluid to flow through the intravenous metering device outlet 53 and the pumping chamber outlet 17 into the pumping chamber 11. Because the pumping chamber inlet ball check 23 is normally positioned in the closed position as shown in FIG. 2 by force of gravity, inversion of the intravenous metering device 1 as shown in FIG. 3 also opens the pumping chamber inlet 15 thereby allowing the flow of liquid to pass through the intravenous metering device inlet 49, up the chamber 31, down the tube 35, into the pumping chamber 11 and up and out the outlet 17. The pumping chamber wall configuration from the inlet 15 is such (as shown) that the liquid passes tangentially into the pumping chamber. It will be noted that the pumping chamber has a tapering smoothly curved cross-sectional configuration from the diaphragm 13 to the outlet 17 so as to provide no sharp corners or recesses in the pumping chamber wall where air can be trapped. Accordingly, during the filling operation with the device being oriented as illustrated in FIG. 3, the fluid fills the intravenous metering device at velocity in a swirling upwardly spiraling path about the projection 29 thereby sweeping out air or other gases present within the intravenous metering device 1 prior to usage of the device. It is of critical importance that such gases be removed from the pumping chamber in order to ensure that precise amounts of fluid are administered to a patient. In the event that gases are present within the pumping chamber 11, the gases, being compressible as contrasted with a liquid, will alter the amount of liquid transferred to the patient during each reciprocation of the reciprocable diaphragm 13. The presence of gases within the pumping chamber 11 is effectively foreclosed by the configuration of the device allowing for the filling with a swirling liquid action at constant high velocity and the employment of the gas retention chamber 31 during normal operation of the device as was more particularly described in the explanation of FIG. 2 of the drawings.

It is obvious that certain changes can be made to the preferred form of the invention as described above. Accordingly, the claims should be given an interpretation commensurate with the scope of the invention as set out in the claims appended hereto.

What is claimed is:

1. A metering device for intraveneous delivery of liquids to a patient comprising a rigid shell defining a pumping chamber and including laterally projecting shoulders for permitting the device to be inserted into and retained by a control unit in an upright position, a diaphragm forming at least a portion of the upper wall of the chamber, an actuator member engaged with said diaphragm and adapted to be reciprocated vertically by said control unit to pump liquid from said pumping chamber, said chamber having a downwardly tapering smoothly curved cross-sectional configuration so as to provide no sharp corners or recesses in the wall of the chamber and terminating in an outlet port at the bottom thereof, an outlet valve yieldably biased to normally close said outlet port, means for disabling said outlet valve by positively moving it and retaining it in a position spaced from said outlet port so as to permit free flow of liquid therethrough, means defining an inlet port at the upper end of said chamber, a valve normally closing said inlet port, and means defining a tangential inlet from said inlet port into said chamber whereby when said device is initially charged with liquid by inverting it and opening the outlet valve with said outlet valve disabling means liquid is caused to flow through said inlet port and tangentially into said chamber wherein it swirls upwardly and through the open outlet port to sweep all air from said chamber.

2. A metering device according to claim 1 wherein said inlet port is oriented so that the liquid is discharged downwardly therefrom when the device is inverted during initial charging of the device with liquid.

3. A metering device according to claim 2 wherein the inlet port lies generally parallel to and spaced from said diaphragm.

4. A metering device according to claim 1 wherein said outlet valve disabling means comprises a vertically extending projection of said diaphragm.

5. A metering device according to claim 4 wherein said projection is downwardly tapered toward said outlet port.

6. A metering device according to claim 1 wherein said diaphragm extends completely across the top of said chamber in a generally horizontal plane.

7. A metering device according to claim 1 wherein said valve at the inlet port comprises a ball check valve normally urged by gravity into sealing relationship with said inlet port.

* * * * *